United States Patent
Contel et al.

(10) Patent No.: US 11,141,490 B2
(45) Date of Patent: Oct. 12, 2021

(54) ANTIBODY-DRUG CONJUGATES BASED ON GOLD COMPOUNDS

(71) Applicants: Research Foundation of the City University of New York, New York, NY (US); Memorial Sloan Kettering Cancer Center, New York, NY (US)

(72) Inventors: Maria Contel, Brooklyn, NY (US); Natalia Curado, Brooklyn, NY (US); Jason Lewis, New York, NY (US); Sophie Poty, New York, NY (US)

(73) Assignees: Research Foundation of the City University of New York, New York, NY (US); Memorial Sloan Kettering Cancer Center, New York, NY (US)

( * ) Notice: Subject to any disclaimer, the term of this patent is extended or adjusted under 35 U.S.C. 154(b) by 114 days.

(21) Appl. No.: 16/503,958

(22) Filed: Jul. 5, 2019

(65) Prior Publication Data

US 2020/0016276 A1 Jan. 16, 2020

Related U.S. Application Data

(60) Provisional application No. 62/697,617, filed on Jul. 13, 2018.

(51) Int. Cl.
| | |
|---|---|
| *A61K 47/68* | (2017.01) |
| *A61K 49/00* | (2006.01) |
| *A61P 35/00* | (2006.01) |
| *A61K 31/555* | (2006.01) |

(52) U.S. Cl.
CPC ........ *A61K 47/6855* (2017.08); *A61K 31/555* (2013.01); *A61K 47/6803* (2017.08); *A61K 49/0021* (2013.01); *A61K 49/0058* (2013.01); *A61P 35/00* (2018.01)

(58) Field of Classification Search
CPC ............ A61K 47/6855; A61K 47/6803; A61K 49/0021; A61K 49/0058; A61K 31/555; A61K 33/242; A61P 35/00
See application file for complete search history.

(56) References Cited

FOREIGN PATENT DOCUMENTS

WO WO 2014/057115 A1 * 4/2014 ............. A61K 47/48

OTHER PUBLICATIONS

Curado, Natalia; The Indispensable Role of Metals in Medical Diagnostics, Therapeutics and Beyond; Gordon Research Conference; Jun. 24-29, 2018.
Curado, Natalia; Synthetic Approaches to Novel Antibody-Gold based Drug Conjugates for Targeted Delivery in Cancer Chemotherapy;—Scientista Symposium. New York, NY. US. Apr. 13-15, 2018.
Contel; Maria; Organometallic compounds as potential anti-cancer agents. Towards targeted therapeutics;—Seminar at the University of Puerto Rico. NIH-RISE Research Seminar, Apr. 20, 2018.
Le Roi; Guillauma; William & Mary's 17th Annual Graduate Research Symposium, Williamsburgh, Virginia, Mar. 16-17, 2018.
Le Roi; Guillauma; International Conference on Biological Inorganic Chemistry Jul. 31-Aug. 4, 2017.
Elie; Benelita; Cancer Chemotherapeutics: Gold(I)-N-heterocyclic Carbene Motifs in Heterometallic Complexes and Antibody Drug Conjugates; International Conference on Biological Inorganic Chemistry; Jul. 31-Aug. 4, 2017—Florianópolis—Brazil.
Le Roi; Guillauma; Novel Antibody-Gold based Drug Conjugates for Targeted Delivery in Cancer Chemotherapy;—American Chemical Society—New York Section. Organometallic Frontiers. Sep. 2016.
Curado, Natalia; Trastuzumab gold-conjugates: synthetic approach and in vitro evaluation of anticancer activities in breast cancer cell lines; Chem. Commun., 2019, 55, 1394-1397.
Matos; Maria; Synthesis and Biological Evaluation of Homogeneous Thiol-Linked NHC*-Au-Albumin and Trastuzumab Bioconjugates; Chem. Eur. J. 2018, 24, 12250-12253.
Agarwal; Paresh, Site-Specific Antibody-Drug Conjugates: The Nexus of Bioorthogonal Chemistry, Protein Engineering, and Drug Development; Bioconjugate Chem. 2015, 26, 176-192.

(Continued)

*Primary Examiner* — Hong Sang
*Assistant Examiner* — Sung Min Yoon
(74) *Attorney, Agent, or Firm* — Peter J. Mikesell; Schmeiser, Olsen & Watts, LLP

(57) ABSTRACT

Antibody-drug-conjugates (ADC) are provided having a structure of:

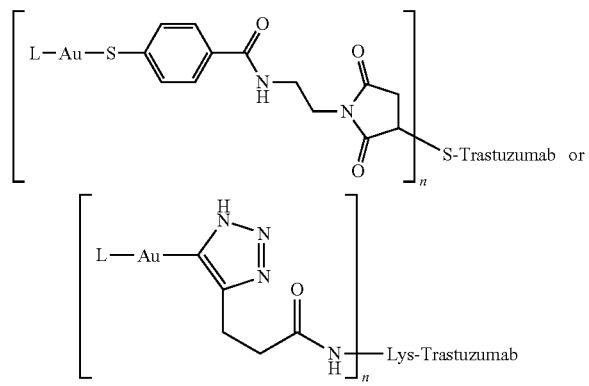

wherein L is $PR_3$ ligand. The ADC has n drug moieties bound to the Trastuzumab antibody such that the ADC has a drug-to-antibody ratio (DAR) between 2 and 4 and the drug moieties are bound to the Trastuzumab antibody through cysteine (S) or lystine (Lys) residues. The disclosed ADCs are particularly useful in treating breast cancer.

6 Claims, 5 Drawing Sheets

(56) References Cited

OTHER PUBLICATIONS

Ban, Hitoshi; Tyrosine Bioconjugation through Aqueous Ene-Type Reactions: A Click-Like Reaction for Tyrosine; J. Am. Chem. Soc. 2010, 132, 1523-1525.
Ban, Hitoshi; Facile and Stabile Linkages through Tyrosine: Bioconjugation Strategies with the Tyrosine-Click; Bioconjugate Chem. 2013, 24, 520-532 Reaction.
Partyka; David; Carbon-Gold Bond Formation through [3 + 2] Cycloaddition Reactions of Gold(I) Azides and Terminal Alkynes; Organometallics, vol. 26, No. 1, 2007.
Zou, Taotao; Chemical biology of anticancer gold(III) and gold(I) complexes; Chem. Soc. Rev., 2015, 44, 8786.
Bertrand; Benoit; A golden future in medicinal inorganic chemistry: the promise of anticancer gold organometallic compounds; Dalton Trans., 2014, 43, 4209.
Porchia, Marina; New insights in Au-NHCs complexes as anticancer agents; European Journal of Medicinal Chemistry 146 (2018) 709-746.
Carter; Paul; Next generation antibody drugs: pursuit of the 'high-hanging fruit'; Nature Reviews; vol. 17 | Mar. 2018.
Chalouni, Cecile; Fate of Antibody-Drug Conjugates in Cancer Cells; Journal of Experimental & Clinical Cancer Research (2018) 37:20.
De Goeij, Bart; New developments for antibody-drug conjugate-based therapeutic approaches; Current Opinion in Immunology 2016, 40:14-23.
Diamantis, Nikolaos; Antibody-drug conjugates—an emerging class of cancer treatment; British Journal of Cancer (2016) 114, 362-367.
Ducry, Laurent; Antibody-Drug Conjugates: Linking Cytotoxic Payloads to Monoclonal Antibodies; Biooonjugate Chem. 2010, 21, 5-13.
Garcia-Alonso, Sara; Resistance to Antibody-Drug Conjugates; Cancer Res; 78(9) May 1, 2018.
Kaplon, Helene; Antibodies to watch in 2019, mAbs; vol. 11, 2019.
Lambert, John; Drug-conjugated monoclonal antibodies for the treatment of cancer; Current Opinion in Pharmacology 2005, 5:543-549.
Lambert, John; Antibody-Drug Conjugates for Cancer Treatment; Annu. Rev. Med. 2018. 69:191-207.
Lu, Jun; Linkers Having a Crucial Role in Antibody-Drug Conjugates; Int. J. Mol. Sci. 2016, 17, 561.
Nasiri, Hadi; Antibody-drug conjugates: Promising and efficient tools for targeted cancer therapy; J Cell Physiol. 2018;233:6441-6457.
Panowski, Siler, Site-specific antibody drug conjugates for cancer therapy; mAbs 6:1, 34-45; Jan./Feb. 2014.
Polakis, Paul; Antibody Drug Conjugates for Cancer Therapy; Pharmacol Rev 68:3-19, Jan. 2016.
Rodrigues, Tiago; Development of Antibody-Directed Therapies: Quo Vadis?; Angew. Chem. Int. Ed. 2018, 57, 2032-2034.
Schumacher, Dominik; Current Status: Site-Specific Antibody Drug Conjugates, J Clin Immunol (2016) 36 (Suppl 1):S100-S107.
Sussman, D.; Engineered cysteine antibodies: an improved antibody-drug conjugate platform with a novel mechanism of drug-linker stability; Protein Engineering, Design & Selection, 2017, vol. 31 No. 2, pp. 47-54.
Thomas, Anish; Antibody-drug conjugates for cancer therapy; Lancet Oncol 2016; 17: e254-62.
Nardon, C. er al.; Gold Complexes for Therapeutic Purposes: an Updated Patent Review (2010-2015); Current Medicinal Chemistry; 2016; pp. 3374-3403; vol. 23, No. 29.

\* cited by examiner

| | [AuCl(PPh$_3$)] | [Au(mba)(PPh$_3$)] | Trastuzumab | AF |
|---|---|---|---|---|
| MCF-7 (A) | 3.57±0.33 | 2.36±0.32 | >60 µM | 4.09±0.07 |
| BT-474 (B) | 3.32±0.10 | 3.51±0.16 | >60 µM | 3.94±0.33 |
| MCF-10a (C) | 18.94±1.30 | 5.52±0.36 | >50 µM | 3.19±0.45 |
| EC$_{50}$ (C)/EC$_{50}$ (A) | 5.30±0.61 | 2.34±0.35 | 0.83±0.13 | 0.78±0.11 |
| EC$_{50}$ (C)/EC$_{50}$ (B) | 5.70±0.43 | 1.57±0.13 | 0.83±0.13 | 0.81±0.31 |

| | 1 | 4 | Tras-1 | Trans-4 |
|---|---|---|---|---|
| MCF-7 (A) | 38.76±4.85 | 2.73±0.86 | 2.67±0.70 | 0.63±0.05 |
| BT-474 (B) | 23.28±0.31 | 0.81±0.01 | 1.73±0.17 | 0.32±0.01 |
| MCF-10a (C) | 44.57±5.15 | 6.77±0.67 | 5.69±0.45 | 4.04±0.20 |
| EC$_{50}$ (C)/EC$_{50}$ (A) | 1.15±0.20 | 2.48±0.82 | 2.13±0.58 | 6.41±0.60 |
| EC$_{50}$ (C)/EC$_{50}$ (B) | 1.91±0.22 | 8.35±0.83 | 3.29±0.41 | 12.63±0.74 |

FIG. 5

ANTIBODY-DRUG CONJUGATES BASED ON GOLD COMPOUNDS

CROSS-REFERENCE TO RELATED APPLICATIONS

This application claims priority to and is a non-provisional of U.S. Patent Application 62/697,617 (filed Jul. 13, 2018), the entirety of which is incorporated herein by reference.

STATEMENT OF FEDERALLY SPONSORED RESEARCH OR DEVELOPMENT

This invention was made with government support under grant numbers 1SC1CA182844; 2SC1GM127278-05A1 and P30 CA08748 awarded by the National Institute of Health—National Institute of General Medical Sciences. The government has certain rights in the invention.

BACKGROUND OF THE INVENTION

Antibody-drug conjugates (ADCs) represent a promising therapeutic approach for cancer chemotherapy. These conjugates combine the antigen-targeting specificity of monoclonal antibodies (mABs) with the cytotoxic potency of chemotherapeutics. Human tumor cells have unique or overexpressed tumor-specific antigens and mABs can specifically bind to these antigens. Monoclonal antibodies have been used as anticancer agents as they can induce an immunological response or inhibit cellular signaling pathways. However, therapeutic efficacy is limited by the cell death effect that the mAB may generate and addition of small molecule cytotoxic payloads has shown to increase the efficacy.

Since the vast majority of cytotoxic drugs do not discriminate tumor and healthy tissues, the use of mAbs as targeting vehicles gives rise to more selective chemotherapeutic treatments. Two ADCs were approved by the US Food and Drug Administration (FDA) and the European Medicine Agency (EMA), ADCETRIS® (brentuximab vedotin) in 2011 and KADCYLA® (Trastuzumab emtansine or T-DM1) in 2013. More recently in 2017, inotuzumab (BESPONSA®) and gemtuzumab ozogamicin (MYLOTARG®) have also been approved by the FDA. In addition, over 65 ADCs (in 2017) are in the clinical pipeline. This disclosure focuses on new generations of ADCs based on site-specific conjugation and a different type of payload which would minimize their high cost-of-goods.

It is clear that there is a need to develop ADCs for different types of cancer and also ADCs based on more selective (less toxic to healthy tissues and organs) payloads than those described. Recently, a number of metal-based drugs and most specifically gold-based compounds that are known to be highly cytotoxic but selective towards cancer cells, have been described. The commercial product RIDAURA® (gold compound Auranofin) does not have severe side effects in humans despite of being a medication designed for a chronic disease (rheumatoid arthritis) and therefore taken during prolonged periods of time (as opposed to chemotherapeutics for cancer usually taken during specific periods). The most severe side effects affecting 26-40% of patients are diarrhea and rashes. Auranofin has been recently approved (2018) by FDA for clinical trials in amebiasis (parasitic disease) with a dose of up to 21 mg a day (adults) for periods longer than 21 days.

In terms of cytotoxic payloads, very few ADCs based on metal-compounds as cytotoxic loads have been described. Gold(I) compounds have emerged as potential anticancer chemotherapeutics with Auranofin (AF) ([(2R,3R,4S,5R,6S)-3,4,5-tris(acetyloxy)-6-{[(triethyl-λ5-phosphanylidene)aurio]sulfanyl}-oxan-2-yl]methyl acetate, a compound containing the [AuPEt$_3$]$^+$ fragment) being evaluated in clinical trials. AF is known for its redox enzymes inhibitory and ROS scavenging properties. The first ADC based on a N-heterocyclic carbene gold fragment conjugated to an engineered Trastuzumab antibody, Thiomab, was reported recently. With an GI$_{50}$ in the low micromolar range, the anti-proliferative activity of this ADC in HER2 positive breast cancer cell line showed a promising moderate improvement as compared to the gold-complex drug. However, the direct conjugation of the gold atom to the free cysteine of Thiomab (Au—S-cysteine bond) may pose in vivo stability issues. Linkers in ADC constructs do not only serve the purpose of bridging the antibody and the cytotoxic drug, but also play a relevant role in the ADC stability during preparation, storage and systemic circulation period. They can also facilitate intracellular targeted release by inclusion of appropriate functionalities.

The discussion above is merely provided for general background information and is not intended to be used as an aid in determining the scope of the claimed subject matter.

SUMMARY

In a first embodiment, a composition of matter is provided. The composition of matter comprising:

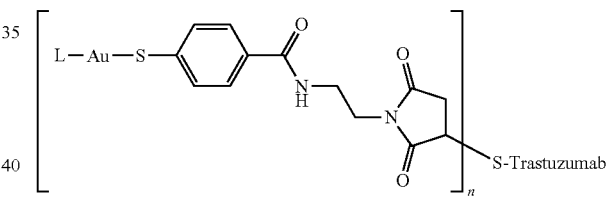

wherein L is PR$_3$ where R is alkyl or aryl or NHC heterocyclic carbene; the composition of matter has n drug moieties bound to the Trastuzumab antibody such that the composition of matter has a drug-to-antibody ratio (DAR) between 2 and 4 and the drug moieties are bound to the Trastuzumab antibody through cysteine residues.

In a second embodiment, a composition of matter is provided. A composition of matter comprising:

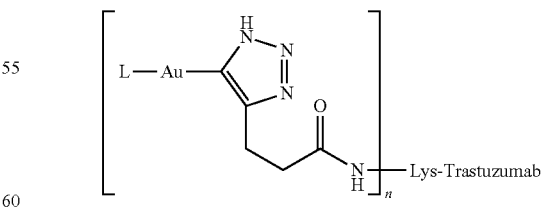

wherein L is PR$_3$ where R is alkyl or aryl or NHC heterocyclic carbene; the composition of matter has n drug moieties bound to the Trastuzumab antibody such that the composition of matter has a drug-to-antibody ratio (DAR) between 2 and 4 and the drug moieties are bound to the Trastuzumab antibody through lystine residues.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a table showing the results of cell viability assays on various compounds.

DETAILED DESCRIPTION OF THE INVENTION

This disclosure pertains to the development of novel targeted chemotherapeutics for the treatment of cancer based on gold compounds. This disclosure improves the delivery of these drugs so that they can be efficiently released at the specific tumor site without affecting healthy tissues.

The conjugation of metallodrugs to ABs has been neglected and there is enormous potential in this area with the resurgence of metal-based drugs as potential cancer chemotherapeutics. The disclosed system aims to combine the potential of ABs with highly cytotoxic and effective gold(I) compounds into a single bioconjugate (ADC) or chimeric hybrid. The synthetic procedures for the connection to the antibody are easier than with other cytotoxic payloads. The syntheses described here can be applied to a variety of linkers amenable to bioconjugations to different monoclonal antibodies and biomolecules.

In one embodiment, an ADC is provided having a structure of:

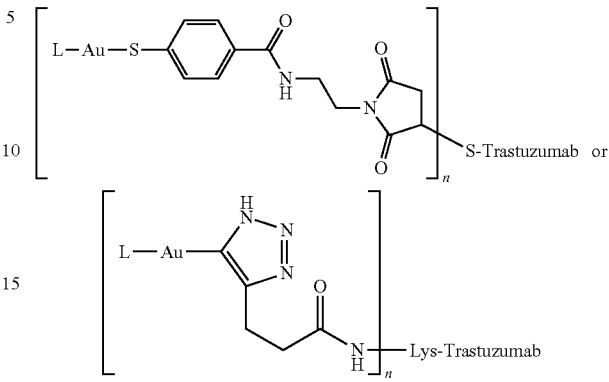

wherein L is $PR_3$ ligand, wherein R is alkyl (e.g. methyl, ethyl or propyl) or aryl (e.g. phenyl or methylphenyl) or a N-heterocyclic carbene (NHC) such as benzimidazole, imidazole or imidazoline. In one embodiment, the R is $PPh_2R'$ where R' is a functionalized aryl group containing a luminescent boron-dipyrromethene (BODIPY) fragment. Such BODIPYs are commercially available. The ADC has n drug moieties bound to the Trastuzumab antibody such that the ADC has a drug-to-antibody ratio (DAR) between 2 and 4 and the drug moieties are bound to the Trastuzumab antibody through cysteine (S) or lysine (Lys) residues as shown.

This disclosure describes synthetic procedures to prepare antibody drug conjugates containing gold compounds. While these strategies can be applied to different antibodies, the specific example described herein is for Trastuzumab (HERCEPTIN®, Genentech) a humanized IgG1 mAb which has been exploited successfully as both a therapeutic agent and radiotracer. Its main use in cancer therapy has been for breast cancer. The disclosed in vitro preliminary data is for breast cancer cell lines.

More specifically, this disclosure provides for the preparation of gold(I)-compounds that are amenable to efficient bioconjugation with monoclonal antibodies via activated ester or maleimide linkers. New Trastuzumab-gold conjugates were synthesized and fully characterized. These bioconjugates are significantly more cytotoxic (sub-micromolar range) to HER2-positive breast cancer cells than the gold complexes and Trastuzumab. This disclosure describes the preparation of gold compounds containing the $[Au(PPh_3)]^+$ motif and a linker. This disclosure stands as a proof-of-concept for the efficient and versatile bioconjugation of gold complexes to mAbs.

Figure 1:
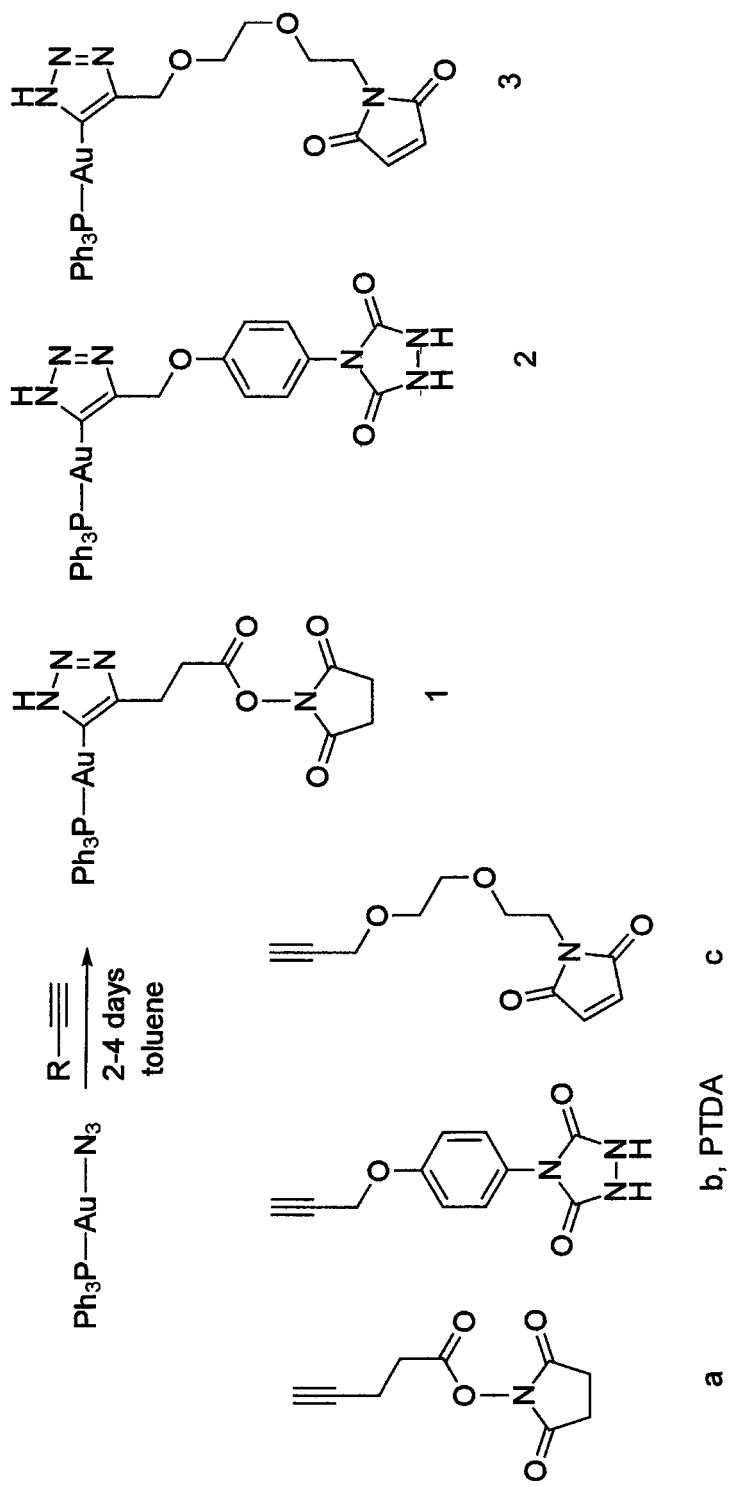
FIG. 1 is a synthetic scheme showing the synthesis of three drugs for subsequent conjugation.
Figure 2:
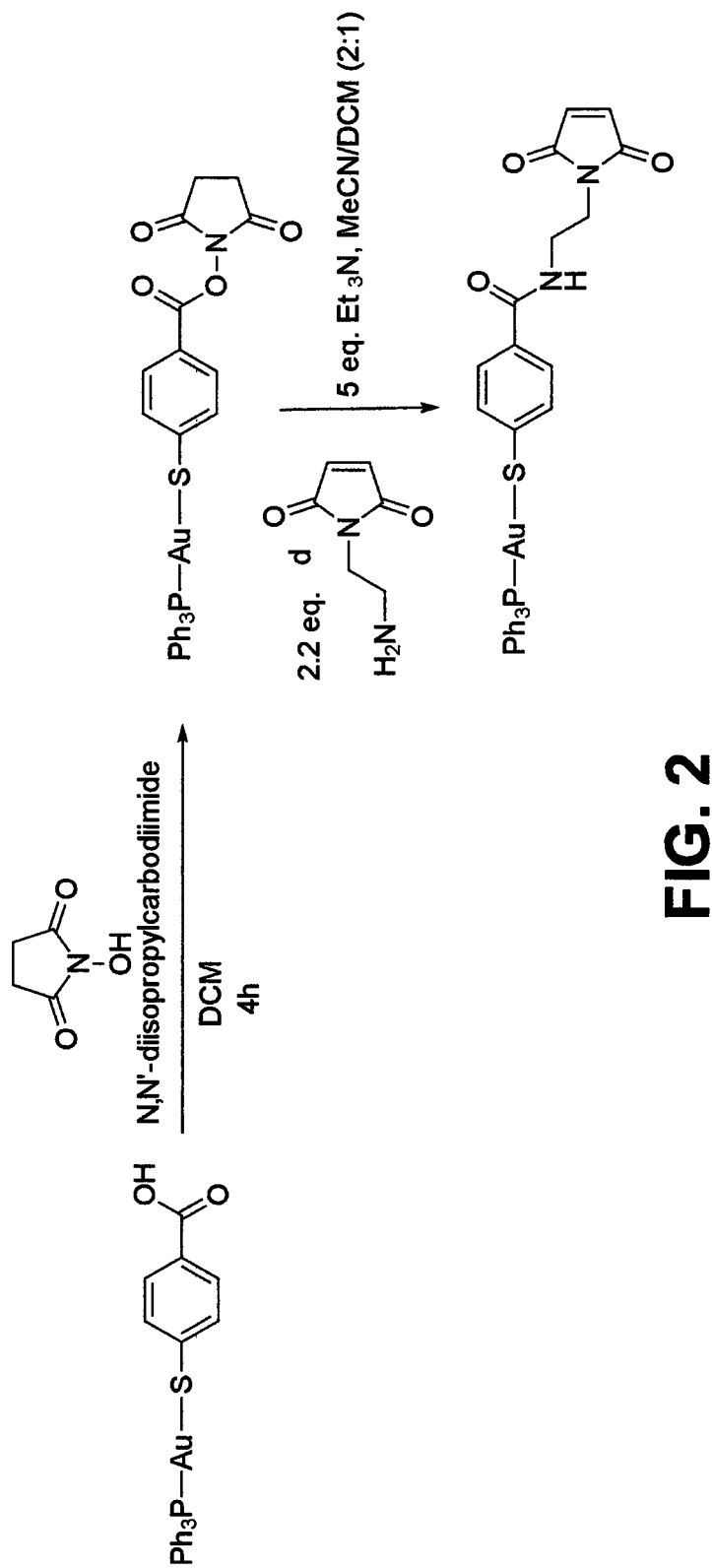
FIG. 2 is a synthetic scheme showing the synthesis of one drug for subsequent conjugation.

The preparation of the new linkers containing the $[AuPPh_3]^+$ fragment (compounds 1-4) are depicted in FIG. 1. All linkers employed are commercially available with linker b (PTDA) already described for the preparation of ADCs. The first strategy (A) is based on a copper-free cycloaddition reaction between a linker terminal alkyne and gold azide complex. This reaction was first described by Gray et al. in 2007 (Organometallics, 2007, 26, 183), and employed in the preparation of peptides containing gold. The second strategy (FIG. 2) is based on amide bond formation between a linker with a terminal amine and a gold thiolate compound containing a free carboxylate group ([Au(mba)(PPh_3)]). The second method is simpler and more environmentally friendly than the cycloaddition reactions as it involves shorter reaction times at room temperature and less toxic reagents.

Compounds 1-4 were obtained in moderate yields (30-60%) and were fully characterized. Compound 3 could only be characterized by elemental analysis and partially by NMR, as it is insoluble in most organic and inorganic solvents and only slightly soluble in DMSO. Compounds 1-4 stability profile in solution (either in $d_6$-DMSO, or mixtures $d_6$-DMSO:PBS-$D_2O$ in a ratio 3:1) was studied by $^1H$ and $^{31}P\{1H\}$ NMR spectroscopy. Compounds 2 and 4 remained intact in $d_6$-DMSO for up to 14 and 40 days, respectively. Compound 4 was equally stable in $d_6$-DMSO: PBS-$D_2O$. Compound 1 (containing hygroscopic linker a) displayed the lowest stability, with half-lives of 6 and 5 hours in $d_6$-DMSO and $d_6$-DMSO/PBS-$D_2O$, respectively. However, this stability is sufficient for subsequent bioconjugation reactions.

Two compounds (1 and 4) with two distinct groups amenable for bioconjugation and good solubility were selected for bioconjugation reactions to the anti-HER2 antibody, Trastuzumab. Trastuzumab (HERCEPTIN®, Genentech) is a humanized IgG1 mAb, which has been exploited successfully as a targeting vector for both therapeutic agent and radioactive isotopes. Its main application lies in the treatment of HER2 positive cancers either alone, or in combination with chemotherapy, hormone blockers or tyrosine kinase inhibitors. Overexpression of HER2 correlates with increased tumor aggression and metastatic potential.

Figure 3:
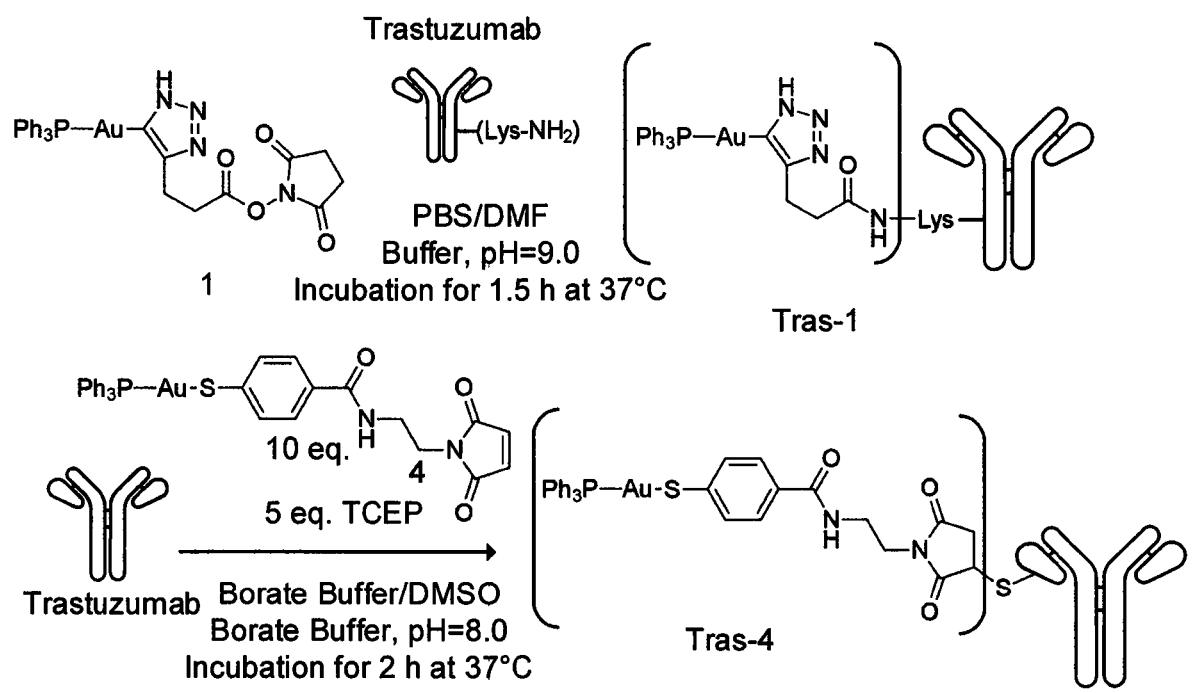
FIG. 3 is a synthetic scheme showing conjugation of two drugs to a respective antibody.

Referring to FIG. 3, compound 1 activated N-hydroxysuccinimide (NHS) ester moiety can react with Trastuzumab available lysine residues while compound 4 maleimide moiety can react with Trastuzumab cysteine residues available after reduction of Trastuzumab inter-chain disulfide bonds. The selectivity of the conjugation method is of primary importance as non-site selective methods will result in heterogeneous ADC mixtures with a broad range of properties (e.g. binding potency, stability). Due to the high number of lysine accessible in a typical antibody (up to 20), lysine conjugation results in heterogeneous ADC population with a broad range of drug-to-antibody ratio (DAR) and a plethora of potential regioisomers. Methods for site-selective conjugation were evaluated to overcome ADCs' heterogeneity and include the reduction of antibody inter chain disulfide bound to provide free cysteine.

Two new antibody gold-based conjugates (AGCs), Tras-1 and Tras-4, were successfully obtained using the lysine and cysteine conjugation strategies with yields of 55% and 70% respectively. Tras-1 and Tras-4 were characterized by MALDI-TOF and size exclusion HPLC. Lysine conjugation resulted in Tras-1 with a DAR of 2.7-3.2 while conjugation through cysteine resulted in Tras-4 with a DAR of 2.7. The molar ratios of the DAR may be measured by LC/MS or by MALDI TOFF MS. DARs strongly influence the efficacy of ADCs. Low DARs can result in reduced potency of the ADC while high DARs can result in increased pharmacokinetic of the ADC. To mitigate such effects, a DAR between 2 and 4 was targeted for the AGCs. Furthermore, Tras-1 and Tras-4 were obtained with purity greater than 95%.

Figure 4:
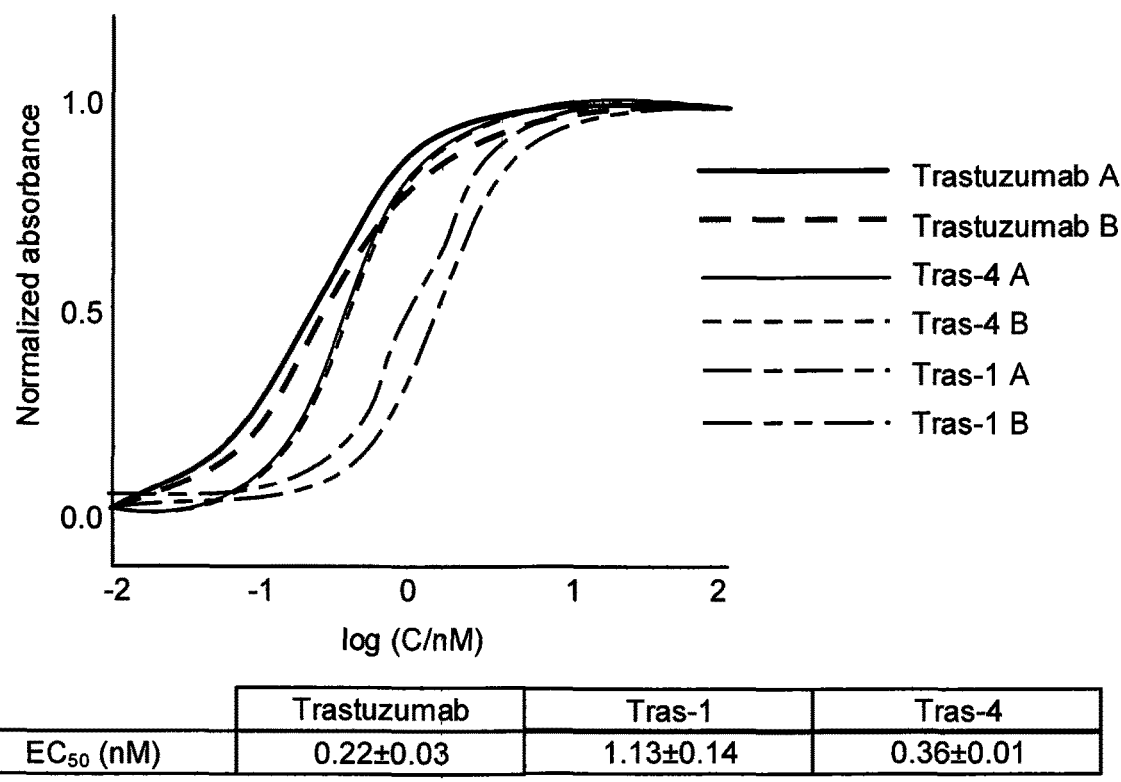
FIG. 4 is a graph depicting results of an ELISA assay for Tras-1 and Tras-4 and HER2.

Binding affinity of Tras-1 and Tras-4 for HER2 was evaluated in an ELISA assay (FIG. 4). Compared to unmodified Trastuzu-mab ($EC_{50}$=0.22±0.03 nM), both Tras-1 and Tras-4 showed a slight decrease in binding affinity for HER2 with $EC_{50}$ of 1.13±0.14 and 0.36±0.01 nM, respectively. As expected, Tras-1 showed the lowest affinity for HER2. This slight decrease in affinity is hypothesized to result from the non-site selective modification of the Trastuzumab antibody through lysine conjugation. Modification through cysteine conjugation (Tras-4) resulted indeed in a much more moderate decrease in affinity.

Even though, the AGCs demonstrated a decrease affinity for HER2, their binding affinity is still in the same range as unmodified Trastuzumab. The stability of the AGCs was studied in human serum over a 7 day period. The presence of unconjugated gold was evaluated by ICP-OES. No release of gold was observed up to 7 days, confirming the stability of the AGCs. See FIG. 5.

Cell viability assays were carried out to investigate the anti-proliferative effect of the AGCs. The cytotoxicity of soluble gold compounds 1, 2 and 4, gold starting materials [AuCl(PPh$_3$)] and [Au(mba)(PPh$_3$)], unmodified Trastuzumab and new AGCs Tras-1 and Tras-4 were evaluated on HER2-positive breast cancer cells (MCF-7 and BT-474) and on a non-cancerous human breast cell line (MCF-10A). Auranofin was used for comparative purposes. The main results are collected in FIG. 5 and the results for compound 2 can be found in Table 1). Cells were incubated with the compounds for 72 hours and viability was assessed with Presto Blue. Starting materials [AuCl(PPh$_3$)] and [Au (mba)(PPh$_3$)], were cytotoxic to the breast cancer cell line MCF-7 in the low micromolar range ($EC_{50}$=3.6 and 2.4 µM, respectively) when compared to the values for the healthy cell line MCF-10A. Compound 4 showed a comparable cytotoxicity value ($EC_{50}$=2.7 µM) while compound 1 was ten-times less toxic ($EC_{50}$=38.8 µM). In general, the modification of the gold starting materials by incorporation of linkers amenable to bioconjugation did not disrupt considerably the cytotoxic potential of the gold-complexes. As mentioned before, linkers bring considerable advantages in terms of ADC stability.

TABLE 1

% of Au found on the samples, before and after filtration.

| Name of the sample | Description | Concentration of Au in the sample (mg/L) | % Au |
|---|---|---|---|
| 1 | Control Tras-1 (digestion of the 1 mg/mL crude solution of gold antibody conjugate without filtration) | 0.73 | 93% |
| 2 | Control Tras-4 (digestion of the 1 mg/mL crude solution of gold antibody conjugate without filtration) | 0.83 | 106% |
| 3 | Control Tras-1filtration (digestion of the upper solution of 1 mg/mL crude solution of gold antibody conjugate after filtration) | 0.68 | 88% |
| 4 | Control Tras-1 filtration (digestion of the bottom filtrate of 1 mg/mL crude solution of gold antibody conjugate | 0 | 0% |

TABLE 1-continued

% of Au found on the samples, before and after filtration.

| Name of the sample | Description | Concentration of Au in the sample (mg/L) | % Au |
|---|---|---|---|
| 5 | Control Tras-4 filtration (digestion of the upper solution of 1 mg/mL crude solution of gold antibody conjugate after | 0.80 | 103% |
| 6 | Control Tras-4 filtration (digestion of the bottom filtrate of 1 mg/mL crude solution of gold antibody conjugate after filtration) | 0 | 0% |
| 7 | Digestion of the upper solution after filtration of gold antibody conjugate (Tras-1 or Tras-4) in serum at any time point | Aggregates were formed after all digestion attempts | N/A |
| 8 | Digestion of the bottom filtrate after filtration of gold antibody conjugate (Tras-1 or Tras-4) in serum at any | 0 | 0% |

A gold elemental analysis of the samples was carried out using a Perkin-Elmer Optima 7000 DV spectrometer. The concentration of Au (mg/L) in the sample and the percentage of recovery (% recovery) were reported. The percentage recovery (%) was calculated by using the following equation:

$$\% \text{ recovery} = \left[\frac{C_i - C_a}{C_a}\right] \times 100$$

where $C_i$ and $C_a$ define Au concentration in the measured aqueous phases before and after passing through the filter, respectively. The ICP-OES results revealed the total recovery of Au-based particles in the samples.

The AGCs, Tras-1 and Tras-4, displayed enhanced cytotoxicity (very low micromolar and sub-micromolar range) compared to the gold linkers (1 and 4) or Trastzumab in the HER2-positive MCF-7 and BT-474 cell lines. Tras-4 was significantly more cytotoxic than starting material [Au(mba)PPh₃] in the BT-474 cell line (P less than 0.01, unpaired t-test). Conversely, all the compounds and AGCs demonstrated reduced cytotoxicity to the non-cancerous human breast epithelial cell line MCF-10A. This observation is particularly important in the case of the disclosed AGCs since it indicates a HER2-mediated toxicity. The selectivity of Tras-4 is higher compared to Tras-1, all gold starting materials and Auranofin.

In conclusion, this disclosure demonstrated the preparation antibody-gold based conjugates that incorporate linkers. Two bioconjugation strategies were investigated to other site-specific or random functionalization of the antibody. Importantly, the conjugation of gold compounds to Trastuzumab maintains their affinity toward HER2. The two generated AGCs are significantly more cytotoxic to HER2-positive breast cancer cell lines than the gold-containing linkers and Trastuzumab. For ADCs to be efficacious, their cytotoxicity in cells has to be in the low or sub-nanomolar range. The very promising $EC_{50}$ values (low micromolar and sub-micromolar range) obtained for the new AGCs with a non-optimized payload, the fragment [Au(PPh₃)]⁺, warrant the study of new antibody drug conjugates based on gold-cytotoxic payloads displaying low nanomolar $EC_{50}$ values (such as specific gold-N-heterocyclic carbenes). The synthesis described here are much less complex than those described for the incorporation of conventional payloads. Gold payloads may therefore become competitive in terms of the high cost-of-goods of ADCs. The versatility of the strategies developed will allow the synthesis of a library of gold-AGCs with a range of linkers with variable pharmacological profiles or intracellular release functionalities, enabling the preparation of gold-based biological imaging probes.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Experimental Section

NMR spectra were recorded in a Bruker AV400 (¹H-NMR at 400 MHz, ¹³C {¹H} NMR at 100.6 MHz and ³¹P{¹H} NMR at 161.9 MHz). Chemical shifts (δ) are given in ppm and coupling constants (J) in Hertz (Hz), using CDCl₃, d₆-DMSO or PBS-D₂O as solvent, unless otherwise stated. ¹H and ¹³C NMR resonances were measured relative to solvent peaks considering tetramethylsilane=0 ppm, and ³¹P{¹H} NMR was externally referenced to H₃PO₄ (85%). IR spectra (4000-500 cm⁻¹) were recorded on a Nicolet 6700 Fourier transform infrared spectrophotometer on solid state (ATR accessory). Elemental analyses were performed on a Perkin-Elmer 2400 CHNS/O series II analyzer by Atlantic Microlab Inc. (US). Mass spectra electrospray ionization high resolution (MS-ESI-HR) were performed on a Waters Q-Tof Ultima. The theoretical isotopic distributions have been calculated using enviPat Web 2.0. Abbreviations were used along the Supporting Information for Trastuzumab (Tz) and Auranofin (AF).

Synthesis

[AuCl(tht)], [AuN₃(PPh₃)], [AuCl(PPh₃)], [Au(mba)(PPh₃)], were prepared according to known literature methods. Chemicals were purchased as indicated: H[AuCl₄] (STREM Chemicals), Si(CH₃)₄, PTAD-alkyne (b), PPh₃ and 4-mercaptobenzoic acid (Sigma Aldrich), Tl(acac), N-hydroxysuccinimide and N—N'-diisopropylcarbodiimide (Alfa Aesar) and 2,5-Dioxopyrrolidin-1-yl pent-4-ynoate (Li), 1-(2-(2-(Prop-2-ynyloxy)ethoxy)ethyl)-1H-pyrrole-2,5-dione (c) and 1-(2-aminoethyl)-1H-pyrrole-2,5-dione 2,2,2-trifluoroacetate (d) (Abosyn Chemical Inc.). Trastuzumab (Tz) was obtained from Genentech in its usual clinical formulation (440 mg, lyophilized). Reaction solvents were purchased anhydrous from Fisher Scientific (BDH, ACS Grade) and Sigma-Aldrich, used without further purification, and dried in a SPS machine and kept over molecular sieves (3 Å, beads, 4-8 mesh), otherwise over sodium if necessary. Deuterated solvents were purchased from Cambridge Isotope Laboratories, Inc. and were kept over molecular sieves (3 Å, beads, 4-8 mesh). Celite (Celite 545, Diatomaceous Earth) was purchased from VWR International and used as received.

Synthesis of compound 1 [Au(PPh$_3$)(a)]. [AuN$_3$(PPh$_3$)] (0.065 g, 0.13 mmol) and a (0.028 g, 0.14 mmol) were dissolved in dry toluene and stirred for 2 days at room temperature under nitrogen. The white precipitate was filtered, washed with cold dry toluene and n-pentane, and dried under vacuum to afford a white product (0.050 g, 0.07 mmol) in 55% yield. $^1$H NMR (400 MHz, d$^6$-DMSO, 25° C.): δ(ppm) 14.06 (s, 1H, NH), 7.62-7.34 (m, 15H, H$_{Ar}$), 3.11 (bt, 4H, CH$_2$), 2.80 (bt, 2H, CH$_2$), 2.60 (bt, 2H, CH$_2$), 2.30 (bs, 2H, CH$_2$,). $^{31}$P NMR (161 MHz, d$^6$-DMSO, 25° C.): δ(ppm) 43.24. $^{13}$C{$^1$H} NMR (128 MHz, d$^6$-DMSO, 25° C.): δ(ppm) 173.31 (C=O), 170.64 (2×C$_{Suc}$=O), 168.90 (N—C$_{triaz}$=C) 149.78 (C=C$_{triaz}$—NH), 134.38 (C$_{Ar-PPh3}$), 132.42 (C$_{p-Ar-PPh3}$), 130.04 (C$_{Ar-PPh3}$), 125.87 (C$_{ipso-Ar-PPh3}$), 32.13 (CH), 25.91 (CH), 25.69 (2×CH). MS (ESI): m/z Calcd 696.12. Found: 697.13 [M+H]$^+$. Anal. Calcd. for C$_{27}$H$_{24}$AuN$_4$O$_4$P.H$_2$O: C, 45.45; H, 3.53; N, 7.85. Found: C, 45.61; H, 3.63; N, 7.63.

Synthesis of compound 2 [Au(PPh$_3$)(b)]. Under inert atmosphere, crystalline [AuN$_3$(PPh$_3$)] (0.065 g, 0.13 mmol) and PTAD-alkyne ligand b (0.042 g, 0.18 mmol) were stirred in dry tetrahydrofuran (5 mL) at 45° C. for 4 days. The white solid obtained was filtered, washed with dry diethyl ether and n-hexane, and dried under vacuum to afford the desired product (0.065 g, 0.089 mmol) as a white solid in 68% yield. $^1$H NMR (400 MHz, d$^6$-DMSO, 25° C.): δ(ppm) 14.26 (s, $^1$H, N-HTr), 10.35 (bs, 2H, NH$_{PTAD}$), 7.57-7.54 (m, 15H, H$_{Ar}$), 7.24 (d, 2H, H$_{Ar-PTAD}$), 7.13 (d, 2H, H$_{Ar-PTAD}$) 5.23 (s, 2H, CH$_2$). $^{31}$P{$^1$H} NMR (161 MHz, d$^6$-DMSO, 25° C.): δ(ppm) 43.57. $^{13}$C{$^1$H} NMR (100 MHz, d$^6$-DMSO, 25° C.): δ(ppm) 157.86 (C$_{ipso-PTAD}$), 153.81 (C=O), 153.67 (C$_{ipso-triazole}$) 147.58 (C$_{ipso-triazole}$), 133.91 (C$_{Ar-PPh3}$), 131.96 (p-C$_{Ar-PPh3}$), 129.62 (C$_{Ar-PPh3}$), 129.10 (C$_{ipso-Ar-PPh3}$), 127.60 (C$_{Ar-PTAD}$), 124.23 (C$_{ipso-PTAD}$), 115.03 (C$_{Ar-PTAD}$), 63.84 (CH$_2$). MS (ESI): m/z Calcd. 732.14. Found: 733.14 [M+H]$^+$. Anal. Calcd. for C$_{29}$H$_{25}$AuN$_6$O$_3$P.H$_2$O: C, 46.41; H, 3.49; N, 11.20. Found: C, 46.36; H, 3.49; N, 10.81.

Synthesis of compound 3 [Au(PPh$_3$)(c)]. [AuN$_3$(PPh$_3$)] (0.090 g, 0.18 mmol) and PEG linker c (0.046 g, 0.20 mmol) were suspended in dry toluene and stirred for 2 days at room temperature under nitrogen. The white precipitate was filtered, washed with cold dry toluene and diethyl ether, and dried in vacuo to afford a pale salmon solid (0.070 g, 0.1 mmol) in 54% yield. $^1$H NMR (400 MHz, d$^6$-DMSO, 25° C.): δ(ppm) 14.15 (s, 1H, NH), 7.62-7.40 (m, 15H, H$_{Ar}$), 5.44 (d, 2H, $^3$J$_{HH}$=10.8, CH), 4.56 (t, 4H, $^3$J$_{HH}$=9.2, CH$_2$), 3.57-3.38 (m, 6H, CH$_2$). $^{31}$P{$^1$H} NMR (161 MHz, d$^6$-DMSO, 25° C.): δ(ppm) 43.36. Anal. Calcd. for C$_{29}$H$_{28}$AuN$_4$O$_4$P: C, 48.08; H, 3.90; N, 7.73. Found: C, 47.66; H, 4.05; N, 7.61.

Synthesis of compound 4a [Au(PPh$_3$)(NHS)]: Compound [Au(mba)(PPh$_3$)](0.3 g, 0.49 mmol) was dissolved in dichloromethane (9 mL) under nitrogen. N-hydroxysuccinimide (0.056 g, 0.49 mmol) and N—N'-diisopropylcarbodiimide (77 µL, 0.49 mmol) were added to the previous solution and the resulting suspension was stirred for 4 hours at room temperature. The desired compound was extracted from the crude with water (5×30 mL) and dried over MgSO$_4$. The solution was dried under vacuum and a light yellow solid was recovered in 80% yield (0.278 g). $^1$H NMR (400 MHz, CDCl$_3$, 25° C.): δ(ppm) 7.81 (d, 2H, $^3$J$_{HH}$=7.81, Hmba) 7.69 (d, 2H, 3J$_{HH}$=7.69, Hmba), 7.48-7.58 (m, 15H, H$_{Ar}$), 2.88 (bs, 4H, CH2-Suc). $^{31}$P{$^1$H} NMR (161 MHz, CDCl$_3$, 25° C.): δ(ppm) 38.76.

Synthesis of compound 4 [Au(PPh$_3$)(d)]: The active ester 4a (0.25 g, 0.35 mmol) was dissolved in a mixture of acetonitrile/dichloromethane (2:1), and d (0.2 g, 0.77 mmol) was added to the solution. Then, Et$_3$N (245 µL, 5 eq.) was added dropwise to the previous solution. The suspension was stirred at r.t. for 5 hours, and dried under vacuum afterwards. The crude was dissolved in dichloromethane, and the organic phase collected after extraction with brine solution (4×20 mL). The solution was dried over MgSO$_4$ and the volume of solvent reduced in vacuo to the minimum amount. Column chromatography on silica gel (ethyl acetate) followed by precipitation with diethyl ether/hexane (5:1) yielded the final compound as a pale yellow solid (29% yield). $^1$H NMR (400 MHz, CDCl$_3$, 25° C.): δ(ppm) 7.66 (d, 2H, $^3$J$_{HH}$=7.66, H$_{mba}$), 7.64-7.50 (m, 17H, H$_{mba}$ and H$_{ar}$), 6.74 (bd, 2H, CH—CH maleimide), 6.52 (t, 1H, $^3$J$_{HH}$=4.93, NH(CO)), 3.85-3.82 (m, 2H, CH$_2$), 3.67 (dt, 2H, $^1$J$_{HH}$=3.40, $^3$J$_{HH}$=8.57, CH2) ppm. $^{31}$P{$^1$H} NMR (400 MHz, CDCl$_3$, 25° C.) δ(ppm) 38.23 ppm. $^{13}$C{$^1$H}NMR (100 MHz, CDCl$_3$, 25° C.) δ(ppm) 171.32 (C=O maleimide), 167.66 (C=O amide), 148.27 (4-mba), 134.48 (C$_{Ar-PPh3}$), 134.3 (CH maleimide), 132.59 (1-mba), 132.4 (mba), 131.99 (mba), 129.57 (C$_{Ar-PPh3}$), 129.42 (C$_{Ar-PPh3}$), 126.8 (C$_{Ar-PPh3}$), 39.68 (CH$_2$ close to the amide), 37.65 (CH$_2$ close to maleimide). IR (ATR): ν=3328 (w, amine N—H stretch), 1703 (s, amide C=O) cm$^{-1}$. MS (ESI): m/z Calcd 734.11. Found: 750.31 [C$_{30}$H$_{28}$AuN$_2$O$_2$PS.CH$_3$CN]$^+$. Anal. Calcd. for C$_{30}$H$_{26}$AuN$_2$O$_3$PS: C, 50.69; H, 3.57; N, 3.81; S, 4.36. Found: C, 50.36; H, 3.67; N, 3.46: S, 4.27.

Synthesis of Gold Antibody Drug Conjugates.

Synthesis of Tras-1: The pH of a solution of Tz in PBS buffer (95 µM, about 210 µL) was adjusted to 9 (with a basic solution of Na$_2$CO$_3$ in distilled water). A solution of 1 in dry dimethylformamide (ca. 19 mM) was prepared and added in aliquots of 2 µL to avoid the precipitation of the compound in solution achieving a final concentration of the solvent in solution below 10%. The reaction was incubated at 37° C. for 1.5 h under mild agitation, and purified by size exclusion using PD-10 Columns (GE Healthcare).

Synthesis of Tras-4: To a Tz solution (22.9 µM, ~300 µL) in borate buffer (25 mM NaCl, 1 mM EDTA, 25 mM sodium borate, pH 8.0) were added 10 equiv. of a stock solution of compound 4 in dry DMSO in aliquots of 2 µL to avoid high concentration of DMSO in solution. Next, 5 equiv. of freshly prepared TCEP in PBS (22.9 mM) were added and the reaction incubated at 37° C. for 2 h under mild agitation. Purification of the product was achieved by exclusion using PD-10 Columns (GE Healthcare).

MALDI-TOF spectra of AGCs Tras1 and Tras4 and DAR calculations.

To determine the number of gold-complexes conjugated per antibody, the immunoconjugates were analyzed by MALDI-TOF MS/MS at the Alberta Proteomics and Mass Spectrometry Facility, University of Alberta, Canada. 1 µL of each sample (1 mg/mL) was mixed with 1 µL of sinapic acid (10 mg/ml in 50% acetonitrile:water and 0.1% trifluoroacetic acid). 1 µL of the sample/matrix solution was then spotted onto a stainless steel target plate and allowed to air dry. All mass spectra were obtained using a Bruker Ultraflex MALDI-TOF/TOF (Bruker Daltonic GmbH). Ions were analyzed in positive mode and external calibration was performed by use of a standard protein mixture (Bovine Serum Albumin). It has to be realized that antibodies have up to 20 lysine residues, however, not all of them are available for bioconjugation. In the case of Trastuzumab, antibody drug conjugates with DARs higher than 3.5 are not commonly reported. Bioconjugation reactions were performed for MALDI-TOF as indicated below:

TABLE 2

| | |
|---|---|
| Tras-1: | |
| | a) 1 equiv. Tz + 24 equiv. 1. |
| | b) 1 equiv. Tz + 12 equiv. 1. |
| Tras-4: | |
| | a) 1 equiv. Tz + 10 equiv. 4 + 5 equiv. TCEP. |
| | b) 1 equiv. Tz + 10 equiv. 4 + 10 equiv. TCEP. |

Enzyme-linked immunosorbent assay (ELISA) for binding assays of AGCs Tras1 and Tras4 and Trastuzumab to HER2.

Binding affinity to HER2 receptor was determined by ELISA. A 96-well plate was coated overnight at 4° C. with HER2 (100 µL of a 0.25 µg/mL solution in PBS). One row of wells was coated with PBS only as a negative control. Wells were washed with PBS (×3) and blocked with a 1% BSA solution in PBS (100 µL) at 20° C. for 1 h. Next, the wells were washed with PBS (100 µL×3). Tz and respective AGCs were diluted in PBS yielding the following concentrations: 300 nM, 100 nM, 30 nM, 10 nM, 3.0 nM, 1.0 nM, 0.3 nM, 0.1 nM, 0.03 nM and 0.01 nM (quadruplicates). The dilution series was added, including PBS only and AGC at 30 nM in the absence of HER2 as negative controls. The plate was incubated for 2 h at 20° C. Wells were washed with PBS (100 µL×2) and the detection antibody (100 µL of anti-human IgG, Fab-specific-HRP solution, 1:5000 in PBS) was added followed by incubation for 1 h at 20° C. After the washing step (100 µL×2), freshly prepared TMB solution (50:50 Peroxide Solution ($H_2O_2$)/Peroxide Substrate (TMB)) was added to each well (100 µL) and the reaction was stopped after 20 min by addition of 1 M H2SO4 (100 µL). The colorimetric reaction was measured at 450 nm and the absorption was corrected by subtracting the average of negative controls. Each measurement was done in quadruplicates.

Stability Studies of AGCs Tras-1 and Tras-4

Procedure

100 µL of gold antibody conjugates (1 mg/mL) in PBS (prepared as described in previous sections) were incubated in 900 µL of human serum at 37° C. (triplicate for each gold antibody conjugate). Aliquots of 100 µL were taken at different time points (2 h, 24 h, 48 h, 72 h, 7 d) and dissolved up to 500 µL in MilliQ water (triplicates). The resulting solutions were centrifuged and filtered using 30 kDa Amicon filters for 12 min at 4000 rpm. Two solutions were separated (solution at the upper part of the filter and filtrate at the bottom). Samples were digested with an aqua regia solution of $HNO_3$ (65%): HCl (35%). For those samples showing incomplete digestion by means of the regular procedure stated before, the concentration of nitric acid was adjusted to 5%. Then, sulfuric acid, hydrogen peroxide and heat were used and applied for the later samples. A different attempt of digestion using protease (37° C. overnight) following by aqua regia was also performed. None of the alternative procedures to aqua regia were successful with samples forming aggregates (upper solution in the filter of Tras-1 and Tras-4 in serum at any time point).

Method

The recovery of the gold-based ADCs particles by filtration was evaluated by means of inductively coupled plasma optical emission spectroscopy (ICP-OES). All the experimental points were repeated in triplicates to confirm reproducibility. The average of the three measurements was reported as the final result.

The percentage of recovery (% recovery) was determined by using the equation on the previous section. The elemental analysis for Au distribution was carried out using a Perkin-Elmer Optima 7000 DV spectrometer. Samples were first digested with an aqua regia solution of $HNO_3$ (65%): HCl (35%), and then the concentration of nitric acid was adjusted to 5% to be within the calibration curve range (from 5 ppm to 10 ppb). Calibration solutions were prepared from a certified stock of a gold single element solution (Sigma-Aldrich, TraceCERT®, 999±2 mg/L). The instrument was calibrated using a six-point calibration curve between 0.01 and 5 ppm and checked by three QC samples at the low, middle and high points on the curve. The operating conditions employed for ICP-OES determination were: 1,300 W RF power, 15 L min$^{-1}$ plasma flow, 0.2 L·min$^{-1}$ auxiliary flow, 0.8 L·min$^{-1}$ nebulizer flow, and 0.8 mL·min$^{-1}$ sample uptake rate. Signals at a wavelength of 267.595 nm were monitored. The low limit of quantification was determined to be 0.01 ppm.

Cell viability analysis for all compounds and AGCs described.

MCF7, MCF10A and BT-474 were obtained from the American Type Culture Collection (ATCC) (Manassas, Va.) and cultured in Dulbecco's modified Eagle's medium (DMEM) (Mediatech) supplemented with 10% FBS, 1% NEAA and 1% penicillin-streptomycin (MCF7 AND MCF1 OA) or DME HG/F12K, NEAA, 2 mM glutamine, 10% FBS/PS and incubated at 37° C. and 5% $CO_2$ in a humidified incubator.

Cytotoxic profiles (EC50) of compounds [AuCl(PPh$_3$)], [Au(mba)(PPh$_3$)], 1, 2, 4, Tras-1, Tras-2, Tz, and AF were obtained by assessing the viability of human breast tumor cells MCF7 and BT-474 and non-tumnorigenic human breast cell line MCF10A treated with the appropriate culture medium containing the specific compounds. Concentrations ranged from 100 µM, to 0.1 µM ([AuCl(PPh$_3$)], [Au(mba) (PPh$_3$)], 1, 2, 4 and AF), and 60-20 µM, to 0.001 µM (Tras-1, Tras-2, Tz). After 72 h, cell viability was determined by means of the colorimetric cell viability assay PrestoBlue (Invitrogen, Carlsbad, Calif.) according to the manufacturer's intructions. $EC_{50}$ were fit using GraphPad Prism 7 to best match the experimental data. All compounds were dissolved in DMSO, DMF and 50:50 DMSO/Tryethylene glycol ([AuCl(PPh$_3$)], [Au(mba)(PPh$_3$)], 1, 2, 4 and AF) and PBS (phosphate buffered saline solution) for Tz, Tras-1, Tras-4, with a final concentration of the organic solvent of 0.1% maximum. AF has been described to be stable for longer than 72 hours in DMSO solution at room temperature.

Tables 3 and Table 4 show $EC_{50}$ Values (µM) in MCF7, MCF10A and BT474 cell lines determined with [AuCl (PPh$_3$)] (DMF), [Au(mba)(PPh$_3$)] (0.5:0.5 DMSO/TEG), 1 (DMSO), 2 (DMSO), 4 (0.5:0.5 DMSO/TEG), Tras-1 (PBS), Tras-4 (PBS), Tz (PBS), and AF (DMSO) as control.

TABLE 3

|  | [AuCl(PPh$_3$)] | [Au(mba)(PPh$_3$)] | 1 | 2 | 4 | AF |
|---|---|---|---|---|---|---|
| MCF-7 | 3.57 ± 0.33 | 2.36 ± 0.32 | 38.76 ± 4.85 | 11.63 ± 1.62 | 2.73 ± 0.86 | 4.09 ± 0.07 |
| BT-474 | 3.32 ± 0.10 | 3.51 ± 0.16 | 23.28 ± 0.31 | 57.83 ± 3.58 | 0.81 ± 0.01 | 3.94 ± 0.33 |
| MCF-10A | 18.94 ± 1.30 | 5.52 ± 0.36 | 44.57 ± 5.15 | — | 6.77 ± 0.67 | 3.19 ± 0.45 |

TABLE 4

|  | Tz | Tras-1 | Tras-4 |
|---|---|---|---|
| MCF-7 | >60 | 2.67 ± 0.70 | 0.63 ± 0.05 |
| BT-474 | >60 | 1.73 ± 0.17 | 0.32 ± 0.01 |
| MCF-10A | >50 | 5.69 ± 0.45 | 4.04 ± 0.20 |

Statistical analysis was performed using GraphPad Prism 7. Unpaired two-tailed t-tests were performed to compare $EC_{50}$ values as described below. The $EC_{50}$ values of the AGCs Tras-1 were compared with respect to Tz and compound 1, of AGCs Tras-4 with respect to Tz and compound 4. The value of Tras-4 was compared with respect to the gold(I) starting material [Au(mba)(PPh$_3$)].

TABLE 5

| P values |
|---|
| MCF7 |
| Tras1 vs Tz: unpaired t test, two-tailed P < 0.001 |
| Tras4 vs Tz: unpaired t test, two-tailed P < 0.001 |
| Tras 1 vs 1: unpaired t test, two-tailed P < 0.001 |
| Tras 4 vs 4: unpaired t test, two-tailed P = 0.013 |
| Tras 4 vs {Au(mba)(PPh$_3$)}: unpaired t test, two-tailed P < 0.001 |
| BT474 |
| Tras1 vs Tz: unpaired t test, two-tailed P < 0.001 |
| Tras4 vs Tz: unpaired t test, two-tailed P < 0.001 |
| Tras 1 vs 1: unpaired t test, two-tailed P < 0.001 |
| Tras 4 vs 4: unpaired t test, two-tailed P < 0.001 |
| Tras 4 vs {Au(mba)(PPh3)}: unpaired t test, two-tailed P < 0.001 |

What is claimed is:

1. A composition of matter comprising:

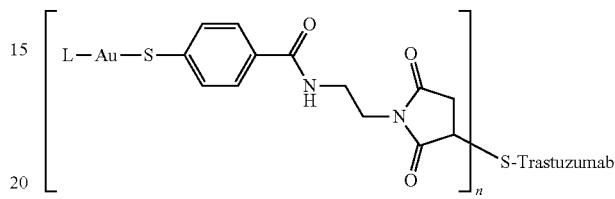

wherein L is PR$_3$ where R is alkyl or aryl or NHC heterocyclic carbene;
the composition of matter has n drug moieties bound to the Trastuzumab antibody such that the composition of matter has a drug-to-antibody ratio (DAR) between 2 and 4 and the drug moieties are bound to the Trastuzumab antibody through cysteine residues.

2. The composition of matter as recited in claim 1, wherein L is PPh$_3$.

3. A method of treating breast cancer in a human patient comprising a step of administering to the human patient the composition of matter as recited in claim 1.

4. A method of treating breast cancer in a human patient comprising a step of administering to the human patient the composition of matter as recited in claim 2.

5. The composition of matter as recited in claim 1, wherein the n is selected such that the drug-to-antibody ratio (DAR) is between 2.7 and 3.2.

6. The composition of matter as recited in claim 1, wherein L is a benzimidazole, or an imidazole.

\* \* \* \* \*